United States Patent
Rudolf et al.

(10) Patent No.: US 10,889,559 B2
(45) Date of Patent: Jan. 12, 2021

(54) METHOD FOR THE PREPARATION OF A MONOTHIOCARBONATE COMPOUND

(71) Applicant: BASF SE, Ludwigshafen am Rhein (DE)

(72) Inventors: Peter Rudolf, Ludwigshafen (DE); Jan-Dirk Arndt, Ludwigshafen (DE); Nicole Holub, Ludwigshafen (DE); Verena Mormul, Ludwigshafen (DE); Indre Thiel, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/633,870

(22) PCT Filed: Aug. 7, 2018

(86) PCT No.: PCT/EP2018/071331
§ 371 (c)(1),
(2) Date: Jan. 24, 2020

(87) PCT Pub. No.: WO2019/034468
PCT Pub. Date: Feb. 21, 2019

(65) Prior Publication Data
US 2020/0299255 A1    Sep. 24, 2020

(30) Foreign Application Priority Data

Aug. 17, 2017 (EP) .................... 17186542

(51) Int. Cl.
*C07D 327/04* (2006.01)
*B01J 21/06* (2006.01)
*C07C 69/96* (2006.01)
*C07C 323/12* (2006.01)

(52) U.S. Cl.
CPC .......... *C07D 327/04* (2013.01); *B01J 21/063* (2013.01); *C07C 69/96* (2013.01); *C07C 323/12* (2013.01)

(58) Field of Classification Search
CPC .... C07D 327/04; B01J 21/063; C07C 323/12; C07C 69/96
USPC ...................................... 549/30, 37
See application file for complete search history.

(56) References Cited

U.S. PATENT DOCUMENTS

| | | |
|---|---|---|
| 2,828,318 A | 3/1958 | Reynolds |
| 3,072,676 A | 1/1963 | Johnson et al. |
| 3,201,416 A | 8/1965 | Johnson et al. |
| 3,349,100 A | 10/1967 | Villa |
| 3,517,029 A | 6/1970 | Johnson |
| 8,673,885 B1 | 3/2014 | Duff |

OTHER PUBLICATIONS

U.S. Appl. No. 16/634,230, filed Jan. 27, 2020, Peter Rudolf, et al.
U.S. Appl. No. 16/639,339, filed Feb. 14, 2020, Peter Rudolf.
U.S. Appl. No. 16/639,204, filed Feb. 14, 2020, Peter Rudolf, et al.
International Preliminary Report on Patentability dated Feb. 18, 2020 in PCT/EP2018/071331 filed Aug. 7, 2018 (with English translation), 11 pages.

*Primary Examiner* — Taylor V Oh
(74) *Attorney, Agent, or Firm* — Oblon, McClelland, Maier & Neustadt, L.L.P.

(57) ABSTRACT

Process for the preparation of a compound with at least one monothiocarbonate group by reacting:—a compound with at least one mercaptoalcohol group and—a dialkylcarbonate, in the presence of a catalyst wherein the catalyst is a salt of a metal selected from group IIIb or IVb of the periodic system.

17 Claims, No Drawings

METHOD FOR THE PREPARATION OF A MONOTHIOCARBONATE COMPOUND

Object of the present invention is a process for the preparation of a compound with at least one monothiocarbonate group by reacting
   a compound with at least one mercaptoalcohol group and
   a dialkylcarbonate
in the presence of a catalyst wherein the catalyst is a salt of a metal selected from group IIIb or IVb of the periodic system.

Monothiocarbonates are useful starting materials for the synthesis of chemical compounds. Different methods for the synthesis of monothiocarbonates are described in the state of the art.

According to the process disclosed in U.S. Pat. No. 3,349,100 alkylene monothiocarbonates are obtained by reacting an epoxide with carbonylsulfide. A synthesis using phosgene as starting material is known from U.S. Pat. No. 2,828,318. Object of U.S. Pat. Nos. 3,072,676 and 3,201,416 is a two-step-process for the preparation of ethylene monothiocarbonates. In a first step mercaptoethanol and chloro carboxylates are reacted to give hydroxyethylthiocarbonate, which is heated in the second step in a presence of metal salt catalyst to the ethylene monothiocarbonate.

According U.S. Pat. No. 3,517,029 alkylene monothiocarbonates are obtained by reacting mercaptoethanol and a carbonate diester in the presence of a catalytically active salt of thorium. Thorium is a rare and expensive element. Any use of thorium in commercial production seems to be problematic due to its radioactivity.

U.S. Pat. No. 3,201,416 discloses a process using alkyl 2-hydroxyethylthiocarbonates as starting material. Alkyl 2-hydroxyethylthiocarbonates undergoes an intramolecular transesterification to give ethylene monothiocarbonate. The process is performed in the presence of a metal salt as catalyst. The metal salt is selected from a list of metals which inter alia includes metals of groups IIIb and IVb of the periodic system.

It was an object of this invention to provide a process for the production of monothiocarbonates which is useful for industrial scale production. The process should not involve expensive starting materials or starting materials of low availability. The process should be easy to perform, should be as economic as possible and give monothiocarbonates in high yield and selectivity.

Accordingly, the above process for the preparation of a compound with at least one monothiocarbonate group has been found.

To the compound with at least one monothiocarbonate group

The monothiocarbonate group is preferably a five-membered cyclic monothiocarbonate group. A five-membered cyclic monothiocarbonate group is a ring system with 5 members, three of them are from the monothiocarbonate —O—C(═O)—S— and the further two members are carbon atoms closing the five-membered cycle.

Preferably, the compound with at least one monothiocarbonate group comprises 1 to 5, more preferably 1 to 2 monothiocarbonate groups and notably 1 monothiocarbonate group.

In a most preferred embodiment, the compound with at least one monothiocarbonate group is a compound of formula I

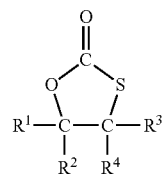

with $R^1$ to $R^4$ independently from each other representing hydrogen or an organic group with up to 50 carbon atoms whereby $R^2$ and $R^4$ and the two carbon atoms to which $R^2$ and $R^4$ are bonded may form a ring system.

In case that any of $R^1$ to $R^4$ represent an organic group, such organic group is preferably an organic group with up to 30 carbon atoms. In a preferred embodiment, such organic group does not comprise further monothiocarbonate groups. The organic group may comprise other elements than carbon and hydrogen. In particular, it may comprise oxygen, nitrogen, sulfur and chloride, for example in form of ether, hydroxy, aldehyde, keto or carboxy, thioether or amino groups.

A preferred organic group is an aliphatic organic group with up to 30 carbon atoms which may comprise oxygen.

A particularly preferred organic group is an alkyl group with 1 to 30 carbon atoms or a group —$CH_2$—O—$R^7$ or —$CH_2$—O—C(═O)—$R^8$ or —$CH_2$—$NR^9R^{10}$ with $R^7$ to $R^{10}$ being an organic group with up to 30 carbon atoms, preferably up to 20 carbon atoms. In particular, $R^7$ to $R^{10}$ represent an aliphatic or aromatic group, which may comprise oxygen, for example in form of ether groups. In a preferred embodiment, $R^7$ to $R^{10}$ represent an alkyl group, an alkoxy group or a poly-alkoxy group. In a most preferred embodiment, $R^7$ to $R^{10}$ represent an alkyl group.

$R^2$ and $R^4$ and the two carbon atoms to which $R^2$ and $R^4$ are bonded may form a ring system, for example a five or six membered ring system. The carbon atoms of the ring system may have substituents such as, for example, alkyl groups or carboxyl groups, such as a carboxylic acid or a carboxylic acid ester group.

In a preferred embodiment two, three or all four of $R^1$ to $R^4$ in formula I represent hydrogen and the remaining groups $R^1$ to $R^4$ represent an organic group.

Most preferably, three or all four of $R^1$ to $R^4$ in formula I represent hydrogen and the remaining group of $R^1$ to $R^4$ represents an organic group.

In a most preferred embodiment all four of $R^1$ to $R^4$ are hydrogen.

To the Reactants

The compound with at least one mercaptoalcohol group comprises preferably 1 to 5, more preferably 1 to 2 mercaptoalcohol groups and notably 1 mercaptoalcohol group.

An example for compounds with more than one mercaptoalcohol group are compounds of the following formula IIa

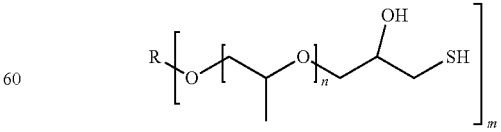

wherein m is an integral number of at least 2, preferably 2 to 5, and R is an m-valent organic group.

Most preferably, the compound with at least one mercaptoalcohol group is a compound of formula IIb

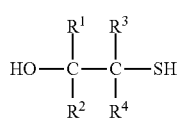

wherein $R^1$ to $R^4$ have the above meanings and the above preferred meanings.

Accordingly, the compound of formula II is mercaptoethanol in case of the most preferred embodiment ($R^1$ to $R^4$ are hydrogen).

The dialkylcarbonate is preferably a compound of formula III

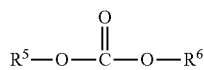

with $R^5$ and $R^6$ independently from each other representing a non-aromatic hydrocarbon group with 1 to 10 carbon atoms or may together form an alkylen bridge comprising 2 to 9 carbon atoms.

Preferably, $R^5$ and $R^6$ represent independently from each other a non-aromatic hydrocarbon group with 1 to 4 carbon atoms or together form an alkylene bridge with 2 or 3 carbon atoms, which is an ethylene or propylene bridge.

In a most preferred embodiment both, $R^5$ and $R^6$, are an alkyl group, notably an ethyl group. Accordingly, the dialkylcarbonate of formula III is diethylcarbonate in the most preferred embodiment.

Mixtures of different dialkylcarbonates and/or dialkenylcarbonates may be used.

To the Catalyst

The catalyst is a salt of a metal selected from group IIIb or IVb of the periodic system.

Preferred are salts of scandium or titanium, in particular salts of titanium.

The anion of the salt may be an inorganic or organic anion.

A suitable inorganic anion is, for example, an anion with sulfur atoms, such as sulfate, or an anion with phosphorous atoms, such as phosphate, an anion with nitrogen atoms, such as nitrate, or a halide such as chloride. A preferred inorganic anion is a halide. Most preferred is chloride.

A suitable organic anion is, in particular, an anion that has at maximum 20 carbon atoms, preferably at maximum 10 carbon atoms. The anion may comprise heteroatoms in non-ionic form, for example oxygen in form of ether or aldehyde groups, sulfur in form of thioether groups and nitrogen in form of amino groups.

Preferably, the organic anion is a monoalcoholate, di- or trialcoholate, a monocarboxylate, di- or a tricarboxylate or a 1,3 dicarbonylenolate, which is in particular acetylacetonate.

The monoalcoholate, dialcoholate or trialcoholate may be an aliphatic or aromatic alcoholate.

In particular, the mono alcoholate is an aliphatic alcoholate such as $R^{11}$—$O^-$ with $R^{11}$ being an organic group with 1 to 20 carbon atoms and which may comprise the above heteroatoms in non-ionic form. In a preferred embodiment $R^{11}$ is a C1 to O10 alkyl group. Preferred alkyl groups are, for example the ethyl group or the isopropyl group; the corresponding anions are ethylate or isopropylate.

In particular, the di- or trialcoholate is an aliphatic alcoholate of formula $R^{12}$ (—$O^-$)$_n$ with $R^{12}$ being a di- or trivalent organic group with 1 to 20 carbon atoms and n being 2 or 3 and which may comprise the above heteroatoms in non-ionic form. In a preferred embodiment it is a dialcoholate with $R^{12}$ being a C1 to O10 alkylene group.

The monocarboxylate, di- or tricarboxylate may be an aliphatic or aromatic carboxylate.

In particular, the monocarboxylate is an aliphatic carboxylate such as $R^{13}$—(C=O)—$O^-$ with $R^{13}$ being an organic group with 1 to 20 carbon atoms which may comprise the above heteroatoms in non-ionic form. In a preferred embodiment $R^{13}$ is a C1 to C10 alkyl group. Preferred alkyl groups are, for example the ethyl group or the isopropyl group; the corresponding anions are acetate or isopropoxylate.

In particular, the di- or tricarboxylate is an aliphatic carboxylate such as dioxalate or a compound of formula $R^{14}$ (—(C=O)—$O^-$)$_m$ with $R^{14}$ being a di- or trivalent organic group with 1 to 20 carbon atoms and with m being 2 or 3 and which may comprise the above heteroatoms in nonionic form. As example for a preferred tricarboxylate citrate may be mentioned. In a further preferred embodiment m is 2 and $R^{14}$ is a C1 to C10 alkylene group. Preferred alkylen groups are, for example the ethylen group or butylene group.

Preferred salts are titanium salts with anions selected from halides, alcoholates or carboxylates.

Most preferred salts are titanium alcoholates, in particular titanium-tetra isopropylate.

To the Reaction

The compound with at least one mercaptoalcohol group and the dialkylcarbonate may be reacted in any molar ratio. In order to avoid too much unreacted compound a preferred molar ratio of mercaptoalcohol groups to dialkylcarbonate is preferably from 0.5:1 to 1:0.5, in particular of 0.7:1 to 1:0.7.

The catalyst may, for example, be used in an amount of 0.0001 to 0.2 mol per mol of mercaptoalcohol groups. Preferably, the catalyst is used in an amount of 0.001 to 0.05 mol per mol of mercaptoalcohol groups. In a most preferred embodiment, the catalyst is used in an amount of 0.005 to 0.05 mol per mol of mercaptoalcohol groups.

The compound with at least one mercaptoalcohol group and the dialkylcarbonate may be reacted at elevated temperature, for example at a temperature of 50 to 150° C., in particular, at 80 to 140° C. The reaction may be performed at reduced or elevated pressure. Usually the reaction is performed at normal pressure. In the reaction alcohol is obtained as a by-product. The alcohol is $R^5$—OH, respectively $R^6$—OH. Preferably, the alcohol is removed during the reaction by distillation.

As at least one of the starting materials is usually liquid an additional solvent is not required. However, if desired, a solvent may be used. Suitable solvents are, for example, aromatics, toluene, xylene, ether, polyether such as glyms, dimthylformamid, THF dioxane, acetonitrile, dimethylsulfoxid.

The reaction may be monitored, for example, via gas chromatography. As soon as the consumption of the starting materials has reached a certain level, the reaction mixture may be cooled down to room temperature and the reaction stops. The obtained product mixture may be worked up by usual methods. In particular, the product mixture may be distilled under vacuum to separate and purify the monothiocarbonate compound obtained.

The process described above is a very economic and effective process and has high suitability for industrial scale production. The process does not involve starting materials of low availability such as thorium. The process gives compounds with monothiocarbonate groups in very high yield and selectivity.

EXAMPLES

Example 1: Catalyst Titanium Tetra Isopropylate

Titanium tetraisopropylate (2.27 g, 0.008 mol) was placed in a 400 mL four neck round bottom flask equipped with a magnetic stirring bar, dropping funnel, thermometer and a reflux condenser. The reaction setup was purged with inert gas, before diethylcarbonate (118.13 g, 1 mol) was added to the catalyst at room temperature. Mercaptoethanol (59.38 g, 0.76 mol) was slowly added over a period of 15 min at room temperature. The bright orange solution was heated to 110-130° C. during which ethanol is removed from the reaction mixture by distillation. The reaction was monitored via gas chromatography analysis. After about 11 h the residual amount of mercaptoethanol was lower than 1%, determined from the peak areas of the gas chromatogramm and the reaction mixture was cooled down to room temperature. Fractioned vacuum distillation of the reaction mixture at 4 mbar and a temperature of the reaction mixture of 45-90° C. resulted in a fraction of the mono thiocarbonate with a purity >98%. The yield of mono thiocarbonate was determined from the peak area of the thiocarbonate peak in the gas chromatogram compared to the area of all peaks (total count). The selectivity of mono thiocarbonate was determined from peak area of the thiocarbonate peak compared to all peaks except the peak of the starting material mercaptoethanol.

Examples 2 to 5

Example 1 has been repeated, but titanium tetraisopropylate has been replaced by the same amount (in mol) of other catalysts named in the Table.

TABLE

Yield and selectivity of mono thiocarbonate from examples 1 to 6

| Example | Catalyst | Yield of thio-carbonate [area %] | Selectivity of thio-carbonate compared to byproducts [area %] |
|---|---|---|---|
| 1 | Titanium tetraiso-propylate | 72 | 87 |
| 2 | Titanium tetrachloride | 28.5 | 74 |
| 3 | Aluminium acetate | 0.1 | 4 |
| 4 | Aluminiumchloride | 4.5 | 32 |
| 5 | Toluene sulfonic acid | 0 | 0 |
| 6 | Boric acid | 0 | 0 |

The invention claimed is:

1. A process for preparing a compound having at least one monothiocarbonate group, the process comprising:
   reacting
      a compound having at least one mercaptoalcohol group, and
      a dialkylcarbonate,
      in the presence of a catalyst,
   wherein the catalyst is a salt of a metal selected from group IIIb or IVb of the periodic table of elements.

2. The process of claim 1, wherein the compound having the at least one monothiocarbonate group is a compound of formula I

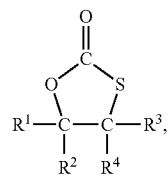

(I)

wherein $R^1$, $R^2$, $R^3$ and $R^4$ each independently represent hydrogen or an organic group comprising up to 50 carbon atoms, and
$R^2$ and $R^4$ and the two carbon atoms to which $R^2$ and $R^4$ are bonded optionally form a ring system.

3. The process of claim 2, wherein the compound having the at least one mercaptoalcohol group is a compound of formula IIb

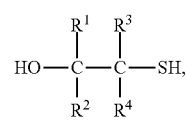

(IIb)

wherein $R^1$, $R^2$, $R^3$ and $R^4$ are defined as in formula I.

4. The process of claim 1, wherein the dialkylcarbonate is a compound of formula III

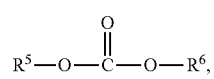

(III)

wherein $R^5$ and $R^6$ each independently represent a non-aromatic hydrocarbon group comprising 1 to 10 carbon atoms or may together form an alkylene bridge comprising 2 to 9 carbon atoms.

5. The process of claim 1, wherein the compound having the at least one mercaptoalcohol group is mercaptoethanol.

6. The process of claim 4, wherein the compound of formula III is diethylcarbonate.

7. The process of claim 1, wherein the catalyst is a salt of scandium or titanium.

8. The process of claim 1, wherein an anion of the salt is a halogenide, an alcoholate or a carboxylate.

9. The process of claim 1, wherein the catalyst is titanium tetra isopropylate.

10. The process of claim 1, wherein the catalyst is a titanium-tetra alcoholate.

11. The process of claim 1, wherein a molar ratio of mercaptoalcohol groups of the compound having at least one mercaptoalcohol group to the dialkyl carbonate is 0.5:1 to 1:0.5.

12. The process according to claim 1, wherein the catalyst is present during the reacting in an amount of 0.005 to 0.05 mol per mol of the mercaptoalcohol groups of the compound having at least one mercaptoalcohol group.

13. The process according to claim 1, wherein the reacting is carried out at a temperature of from 80 to 140° C.

14. The process according to claim 1, wherein the reacting is carried out in the absence of a solvent other than the compound having at least one mercaptoalcohol group and the dialkylcarbonate.

15. The process according to claim 1, further comprising:
removing an alcohol formed while reacting the compound having at least one mercaptoalcohol group and the dialkylcarbonate.

16. The process according to claim 1, further comprising:
during the reacting, removing by distillation an alcohol formed from the compound having at least one mercaptoalcohol group and the dialkylcarbonate.

17. The process according to claim 1, further comprising:
after the reacting, vacuum distilling the monothiocarbonate from a reaction mixture formed by reacting the compound having at least one mercaptoalcohol group and the dialkylcarbonate, wherein the monothiocarbonate obtained by the vacuum distilling has a purity of greater than 98% determined from the peak area of the monothiocarbonate peak in the gas chromatogram compared to the area of all peaks (total count).

\* \* \* \* \*